US012661274B2

(12) United States Patent
Gaston et al.

(10) Patent No.: US 12,661,274 B2
(45) Date of Patent: Jun. 23, 2026

(54) METHOD OF APPLYING FASTENER ELEMENTS FOR DISPOSABLE ABSORBENT GARMENT

(71) Applicant: Attends Healthcare Products, Inc., Greenville, NC (US)

(72) Inventors: William W. Gaston, Greenville, NC (US); Mark Hoff, Oriental, NC (US)

(73) Assignee: Attends Healthcare Products, Inc., Greenville, NC (US)

( * ) Notice: Subject to any disclaimer, the term of this patent is extended or adjusted under 35 U.S.C. 154(b) by 1141 days.

(21) Appl. No.: 16/849,432

(22) Filed: Apr. 15, 2020

(65) Prior Publication Data

US 2020/0237573 A1 Jul. 30, 2020

Related U.S. Application Data

(63) Continuation of application No. 15/017,027, filed on Feb. 5, 2016, now Pat. No. 10,639,213.

(60) Provisional application No. 62/113,103, filed on Feb. 6, 2015.

(51) Int. Cl.
| | |
|---|---|
| *A61F 13/15* | (2006.01) |
| *A61F 13/49* | (2006.01) |
| *A61F 13/56* | (2006.01) |
| *A61F 13/62* | (2006.01) |
| *B32B 37/00* | (2006.01) |

(Continued)

(52) U.S. Cl.
CPC .. *A61F 13/15756* (2013.01); *A61F 13/15723* (2013.01); *A61F 13/49061* (2013.01); *A61F 13/622* (2013.01); *A61F 13/5644* (2013.01);

*A61F 2013/5683* (2013.01); *B32B 37/0076* (2013.01); *B32B 38/04* (2013.01); *B32B 38/1866* (2013.01); *Y10T 156/1062* (2015.01); *Y10T 156/1075* (2015.01); *Y10T 156/1077* (2015.01); *Y10T 156/1089* (2015.01)

(58) Field of Classification Search
CPC .......... A61F 13/15756; A61F 13/15723; A61F 13/56; A61F 13/62; A61F 13/64; A61F 13/66; A61F 13/58; A61F 13/5611; A61F 13/5616; A61F 13/15; A61F 13/49; A61F 2013/5694; A61F 2013/583; A61F 13/5633; A61F 13/5638
See application file for complete search history.

(56) References Cited

U.S. PATENT DOCUMENTS

| | | | |
|---|---|---|---|
| 4,923,456 A | 5/1990 | Proxmire | |
| 4,964,857 A | 10/1990 | Osborn | |

(Continued)

FOREIGN PATENT DOCUMENTS

| | | | | |
|---|---|---|---|---|
| WO | WO-2011096183 A1 * | 8/2011 | ....... A61F 13/49015 |

*Primary Examiner* — Rebecca E Eisenberg
*Assistant Examiner* — Gabriella E Burnette
(74) *Attorney, Agent, or Firm* — Norton Rose Fulbright US LLP

(57) ABSTRACT

Methods of making disposable absorbent articles and disposable absorbent articles that comprise: a first, second, and third fastener elements to a web such that: the first fastener element is spaced from the second fastener element by a first distance along a length of the web; the second fastener element is spaced from the third fastener element by a second distance along the length of the web; and the second fastener element is disposed between the first and third fastener elements.

19 Claims, 4 Drawing Sheets

(51) Int. Cl.
    *B32B 38/04*          (2006.01)
    *B32B 38/18*          (2006.01)

(56)                References Cited

U.S. PATENT DOCUMENTS

| | | | |
|---|---|---|---|
| 5,624,429 A * | 4/1997 | Long | A61F 13/5622 |
| | | | 24/DIG. 11 |
| 7,569,038 B1 | 8/2009 | Salem, Jr. | |
| 9,301,882 B2 | 4/2016 | Sablone | |
| 2008/0091163 A1* | 4/2008 | Fujioka | A61F 13/4942 |
| | | | 2/400 |
| 2010/0004616 A1* | 1/2010 | Nakamura | A61F 13/15756 |
| | | | 604/389 |

* cited by examiner

METHOD OF APPLYING FASTENER ELEMENTS FOR DISPOSABLE ABSORBENT GARMENT

CROSS-REFERENCE TO RELATED APPLICATIONS

This application is a continuation of U.S. patent application Ser. No. 15/017,027, filed Feb. 5, 2016, which claims priority to U.S. Provisional Patent Application No. 62/113, 103, filed Feb. 6, 2015, which are incorporated by reference in their entirety.

FIELD OF INVENTION

The present invention relates generally to disposable absorbent articles such as infant diapers, adult incontinence briefs, pull-up underwear, bladder control pads, bed pads.

BRIEF DESCRIPTION OF RELATED ART

Examples of disposable absorbent articles are disclosed in U.S. Pat. Nos. 4,923,456; 4,964,857; 7,569,038.

Disposable absorbent articles, such as baby diapers, training pants, adult incontinence products and other such absorbent products include a pair of fastening portions on respective extensions configured to connect opposing ends of the article. The fastening portions ensure the opposing ends of the absorbent article remain securely fastened while in use by a wearer. Typically, a peel strength of the fastening portion (e.g., strength required to counteract a normal force) is less than a shear strength of the fastening portion. During use, the extensions of the absorbent article may roll and/or bend, thereby causing one or both fastening portions to separate from its respective extension.

SUMMARY

This disclosure includes embodiments of disposable absorbent articles and methods of making disposable absorbent articles. At least some of the present embodiments increase the structural integrity of the fastening portion (e.g., increase the peel strength) in order to prevent separation of the fastening portion and the absorbent article.

Some embodiments of making the present disposable absorbent articles comprise: joining a first, second, and third fastener elements to a web such that: the first fastener element is spaced from the second fastener element by a first distance along a length of the web; the second fastener element is spaced from the third fastener element by a second distance along the length of the web; and the second fastener element is disposed between the first and third fastener elements; cutting through both of the first fastener element and the web at a first point along the length of the web to define a first end of a first fastener panel; cutting through both of the third fastener element and the web at a second point along the length of the web to define a second end of the first fastener panel; joining the first fastener panel to a chassis of an absorbent article.

In some of the embodiments, joining comprises joining the first fastener panel to an extension portion of a backsheet.

In some of the embodiments, the first, second, and third fastener elements are aligned along a first edge of the web, and the first fastener panel is joined to the chassis along a second edge that opposes the first edge.

In some of the embodiments, the respective lengths of each first, second, and third fastener element is substantially equal.

In some of the embodiments, the article includes a centerline and each respective cut through the web and the first and third fastener members is in a direction perpendicular to the centerline.

In some of the embodiments, during the respective cutting steps, each of the first and third fastener elements is cut substantially in half.

In some of the embodiments, the first distance is substantially equal to the second distance.

In some of the embodiments, cutting through both the third fastener element and the web also defines a first end of a second fastener panel.

Some embodiments of making the present disposable absorbent articles further comprise: joining fourth and fifth fastener elements to the web such that: the fourth fastener element is spaced from the third fastener element by a third distance along the length of the web; the fifth fastener element is spaced from the fourth fastener element by a fourth distance along the length of the web; and the fourth fastener element is disposed between the third and fifth fastener elements; cutting through both the fifth fastener element and the web at a third point along the length of the web to define a second end of the second fastener panel; joining the second fastener panel to the chassis on an opposite side of the chassis than the first fastener panel.

Some embodiments of making the present disposable absorbent articles further comprise coupling an absorbent portion to the backsheet.

In some of the embodiments, the first, second, and third fastener elements are joined with the web by advancing the web in a direction parallel to a centerline of the article.

In some of the embodiments, the first, second, and third fastener elements each has a centerline that is parallel to the centerline of the article.

In some of the embodiments, the first, second, and third fastener elements are cut from a strip of fastener elements before being joined with the web.

In some of the embodiments, the first distance, second distance, third distance, and fourth distance are substantially equal.

Some embodiments of the present disposable absorbent articles comprise: an absorbent article chassis having opposing front and rear waist portions, and a central absorbent portion ending in a longitudinal direction between the front and rear waist portions, a first fastener panel having a first edge coupled to a first side of the rear waist portion, and a second edge configured to overlap a first side of the front waist portion to define a first leg opening on a first side of the central absorbent portion; a second fastener panel having a first edge coupled to a second side of the rear waist portion, and a second edge configured to overlap a second side of the front waist portion to define a second leg opening on a second side of the central absorbent portion; and where the first and second fastener panels each comprises: a first fastener element joined to the fastener panel at the first end; a second fastener element joined to the fastener panel at the second end; a third fastener element joined to the fastener panel such that the third fastener element is spaced apart from each of the first and second fastener elements along a length of the fastener panel.

In some of the embodiments, a length of the second fastener element is substantially equal to the sum of the lengths of a first and third fastener elements.

Some embodiments of the present disposable absorbent articles further comprise: a first extension portion extending between and joined to each of the first side of the rear waist portion and to the first side of the first fastener panel; and a second extension portion extending between and joined to each of the second side of the rear waist portion and the first side of the second fastener panel.

Some embodiments of the present disposable absorbent articles further comprise an absorbent portion on a user-facing surface of the backsheet.

In some of the embodiments, each of the first, second, and third fastener element are disposed on a user-facing surface of the first extension portion.

In some of the embodiments, one or more of the first, second, and third fastener elements include a hook patch.

In some of the embodiments, the first, second, and third fastener elements each has a centerline that is perpendicular to the centerline of the article.

In some of the embodiments, the third fastener element is spaced apart from the first fastener element by a first distance, and the third fastener element is spaced apart from the second fastener element by a second distance that is substantially equal to the first distance.

The term "coupled" is defined as connected, although not necessarily directly, and not necessarily mechanically. Two items are "couplable" if they can be coupled to each other. Unless the context explicitly requires otherwise, items that are couplable are also decouplable, and vice-versa. One non-limiting way in which a first structure is couplable to a second structure is for the first structure to be configured to be coupled (or configured to be couplable) to the second structure. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes" one or more steps possesses those one or more steps, but is not limited to possessing only those one or more steps.

Any embodiment of any of the apparatuses, systems, and methods can consist of or consist essentially of—rather than comprise/include/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Some details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

DESCRIPTION OF ILLUSTRATIVE EMBODIMENTS

Figures 1, 2:
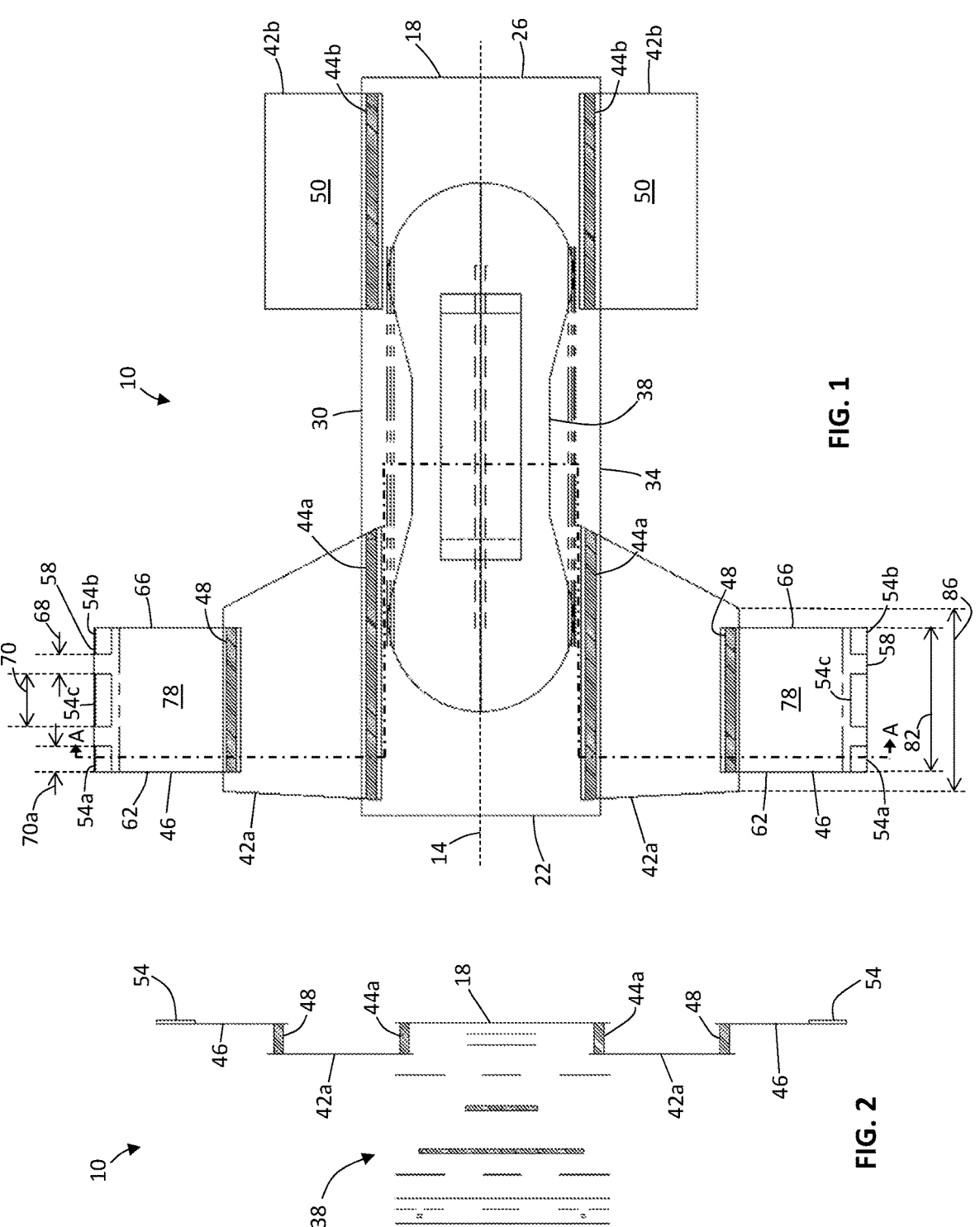
FIG. 1 is a schematic representation of one embodiment of the present disposable absorbent articles.
FIG. 2 is an exploded end view of the article of FIG. 1.

Referring now to the drawings, and more particularly to FIGS. 1 and 2, shown therein and designated by the reference numeral 10 is one embodiment of the present disposable absorbent articles. FIG. 1 shows a schematic top view of article 10. FIG. 2 shows an exploded end view of article 10. In this embodiment, absorbent article 10 is configured as a diaper; in other embodiments, the present absorbent articles can be configured as training pants, adult incontinence products and other such absorbent products having a single- or multi-piece chassis.

Article 10 may be characterized by and described relative to a longitudinally-extending centerline 14. As shown in FIG. 1, article 10 includes a backsheet 18 having a first end 22, a second end 26, and a first side 30 and a second side 34 extending between the ends 22, 26. For example, in use, first end 22 is configured to face a front side of a user and second end 26 is configured to face a back side of the user. Alternatively, first end 22 is configured to face the back side of the user and second end 26 is configured to face the front side of the user.

In some embodiments, article 10 includes an absorbent portion 38. For example, in the embodiment shown, absorbent portion 38 is coupled with backsheet 18. Absorbent portion 38 may be disposed between first end 22 and second end 26 of backsheet 18.

In some embodiments, each side 30 and 34 of backsheet 18 is configured to be coupled with one or more extension portions 42 (e.g., a first extension portion 42a and a second extension portion 42b coupled to each side 30 and 34 of backsheet 18, in the embodiment shown in FIG. 1). One or more first and second extension portions 42a and 42b may be coupled with backsheet 18 at respective bonding portions 44a and 44b with any joining process that provides sufficient strength and durability for the article to function. For example, the extension portions may be joined to the backsheet via ultrasonic bonding or thermal bonding, with an adhesive, and/or with any other suitable joining process and/or material. Alternatively, one or more first and second extension portions 42a and 42b may be integrally formed with backsheet 18. In the embodiment shown, first extension portion 42a is configured to be disposed toward first end 22 of backsheet 18. Second extension portion 42b is configured to be disposed toward second end 26 of backsheet 18. For example, first extension portion 42a is disposed closer to first end 22 than second extension portion 42b, and vice versa. In some embodiments, each of first and second extension portions 42a and 42b extend laterally in a direction away from centerline 14.

In some embodiments, first extension portion 42a is configured to be coupled with a fastener panel 46. For example, fastener panel 46 may be configured to be coupled with first extension portion 42a at a bonding portion 48 with any joining process that provides sufficient strength and durability for the article to function. For example, fastener panel 46 may be joined to extension portion 42a via ultrasonic bonding or thermal bonding, with an adhesive, and/or with any other suitable joining process and/or material. Alternatively, fastener panel 46 may be integrally formed with first extension portion 42a and/or backsheet 18. In some embodiments, fastener panel 46 includes a flexible non-woven and/or an elasticized non-woven laminate. Fastener panel 46 may extend laterally in a direction away from centerline 14, as shown in FIG. 1. Fastener panel 46 is configured to be coupled to second extension portion 42b during use. For example, one or more of fastener panel 46, first extension portion 42a, and/or second extension portion 42b are configured to extend around a side of a user and such that first extension portion 42a, fastener panel 46, second extension portion 42b, and/or backsheet 18 cooperate to define an opening configured to receive a leg of the user. For example, when article 10 is fitted to the user, article 10 is configured to define a leg opening on each side 30 and 34 of backsheet 18 when each fastener panel 46 is coupled to a respective second extension portion 42b. In some embodiments, fastener panel 46 is configured to overlap at least a portion of second extension portion 42b. For example, fastener panel 46 overlaps an inner-facing surface 50 of second extension portion 42b. Alternatively, fastener panel 46 may overlap an outer-facing surface (e.g., opposite inner-facing surface 50).

In some embodiments, each fastener panel 46 includes a plurality of fastener elements 54. In the embodiment shown, each fastener element 54 includes a centerline that is parallel to centerline 14 of article 10. Fastener elements 54 may be coupled to fastener panel 46 along an outer edge 58 thereof, as shown in FIG. 1. Fastener panel 46 may include any appropriate number of fastener elements 54, such as three fastener elements 54. In some embodiments, fastener panel 46 includes a respective first and second fastener element 54a and 54b at a first end 62 and a second end 66 of outer edge 58 of fastener panel 46. Fastener panel 46 may include any appropriate number of fastener elements 54 between fastener elements 54a and 54b. For example, in the embodiment shown, fastener panel 46 includes a third fastener element 54c between fastener elements 54a and 54b. In some embodiments, each fastener element 54 is separated by a length 68 from another fastener element 54. Length 68 ranges from 0.5 inches to 1.5 inches, such as 1 inch. Prior to assembly, each fastener element 54 includes substantially the same length 70. As discussed in further detail below, length 70 may be shortened (e.g., a length 70a) based on the position of the respective fastener element 54 on fastener panel 46. In some embodiments, each fastener element 54a and 54b at respective first end 62 and second end 66 of outer edge 58 has length 70a (e.g., measured in a direction parallel to centerline 14) half as long as length 70 of each fastener element 54 therebetween, such as fastener element 54c. For example, in some embodiments, third fastener element 54b includes length 70, such as 2 inches. As such, each of first and second fastener elements 54 include a length 70a of 1 inch.

Fastener element 54 is configured to secure fastener panel 46 to second extension portion 42b. For example, in the embodiment where fastener panel 46 overlaps outer-facing surface of second extension portion 42b, fastener elements 54 are disposed on an inner-facing surface 78 of fastener panel 46. Alternatively, in the embodiment where fastener panel 46 overlaps inner-facing surface 50 of second extension portion, fastener elements 54 are disposed on an outer-facing surface of fastener panel 46 (e.g., opposite inner-facing surface 78). Fastener elements 54 may include any appropriate material configured to releasably join fastener panel 46 and second extension portion 42b. For example, one or more fastener elements 54 include a hook patch.

Fastener elements 54 and fastener panel 46 may be assembled in any appropriate manner. In the embodiment shown in FIG. 3, a conveyor system 90 is used to assemble article 10. More specifically, conveyor system 90 is configured for receiving, manipulating, and/or conveying a plurality of web inputs (e.g., material from which fastener elements 54 and/or fastener panels 46 are derived). Conveyor system 90 includes one or more spools 98a-d configured for feeding and/or joining the web inputs.

Figure 3:
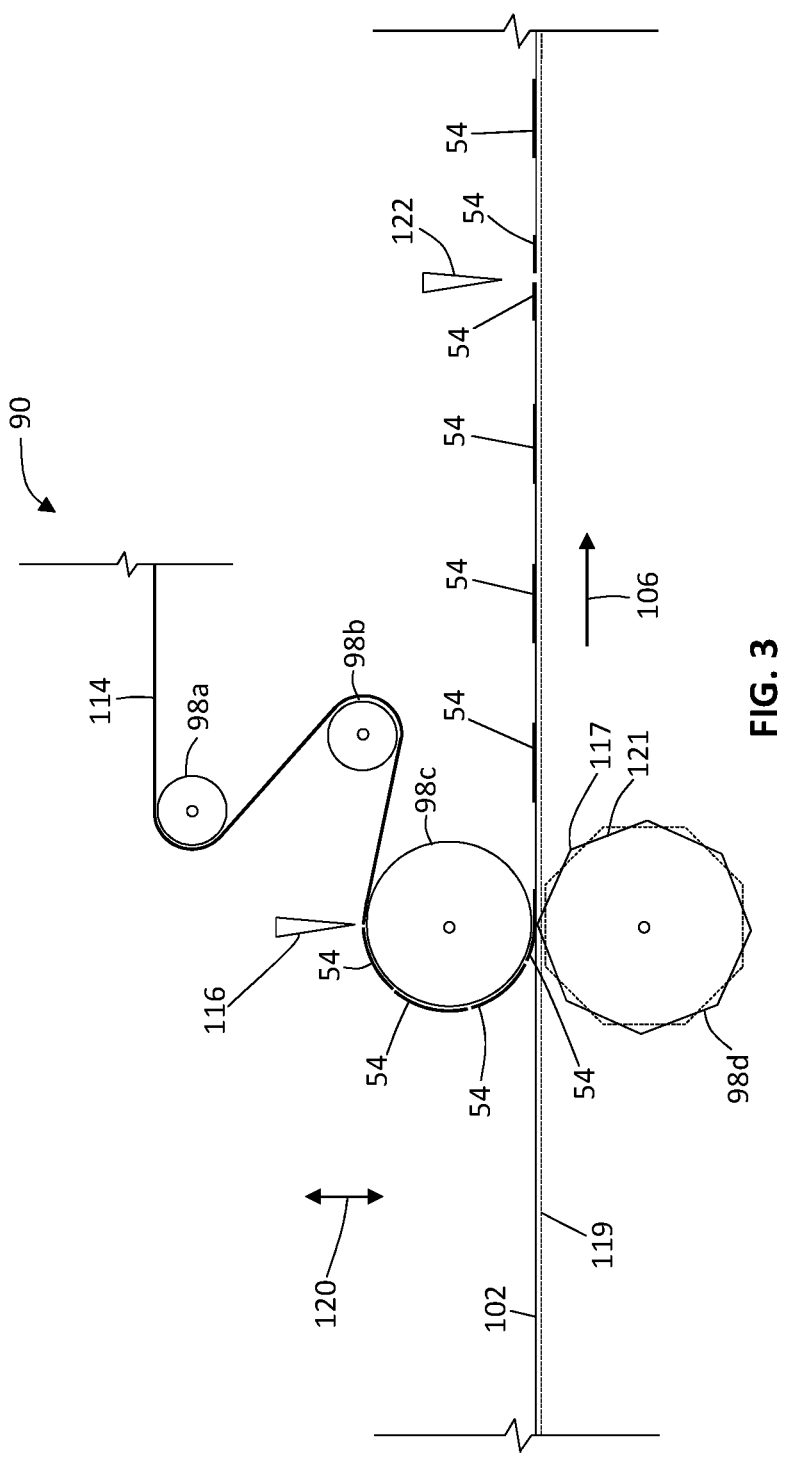
FIG. 3 is a top view of a conveyor system used to assemble the article of FIG. 1.

As shown in FIG. 3, a web 102 of material, such as non-elastic nonwoven from which fastener panels 46 are derived (e.g., cut from), is fed between an anvil (e.g., 98c) and a dauber (e.g., 98d) in a machine direction 106 that is parallel to centerline 14. As used herein, the term "machine" direction refers to the direction at which the component, or more particularly, the material from which fastener elements 54 and/or fastener panels 46 are derived (e.g., cut from), is driven in an assembly line during manufacturing. The term "cross-machine direction" or "cross-directional," on the other hand, refers to a direction 110 (FIG. 4) that is perpendicular to the machine direction. With reference to article 10, cross-machine direction 110 is the direction extending laterally or perpendicularly relative to the centerline 14.

In some embodiments, fastener elements 54 are deposited onto an anvil 98c (e.g., via spools 98a, 98b) while web 102 moves in machine direction 106 such that fastener elements 54, in turn, can be joined to web 102 between anvil 98c and wheel 98d. For example, in the embodiment shown, a web 114 of fastener material is fed via wheels 98a, 98b (e.g., of a taper) and is cut by a blade 116 to define individual fastener elements 54 as the fastener elements are deposited on anvil 98c (e.g., by a cut-at-tape-speed or "CATS" taper). In some embodiments, blade 116 reciprocates in a direction 120 that is normal to web 114 such that a cut is formed through web 114 in cross-direction 110. As shown, blade 116 cuts web 114 such that each fastener element 54 includes length 70. Thereafter, fastener elements 54 may be rolled off spool 98c and joined to web 102. Fastener elements 54 may be temporarily and releasably coupled to anvil 98c in any of various known manners, such as, for example, via a compatible fastening surface on the anvil (e.g., a loop fastening surface if fastener elements 54 comprise hook patches), an adhesive liner from which fastener elements can be removed when pressed to web 102 as described below, and/or any other suitable structure or method for the anvil (98c) to temporarily carry the fastener elements (54))

In the embodiment shown, s anvil 98c rotates (in a counter-clockwise direction, in the embodiment shown), it carries fastener elements 54 into alignment between anvil 98*c* and dauber 98*d*. More particularly, in this embodiment, as anvil 98*c* carries a given fastener element 54 toward dauber 98*d*, dauber 98*d* also rotates (in a clockwise direction, in the embodiment shown) to bring a corresponding vertex 117 (or other suitable protrusion) toward the fastener element and, in doing so, the vertex 117 presses web 102 toward anvil 98*c* and into contact with the given fastener element (such that the web and the fastener element are pressed into contact). When the fastener element and web are pressed into contact, an adhesive (or other suitable fastening structure or process) joins the fastener element to the web.

In the embodiment shown, as dauber 98*d* continues to rotate, a flat or planar portion 121 faces anvil 98*c* (as shown by the dashed line illustrating the rotated position of dauber 98*d*) and opening a gap between dauber 98*c* and anvil 98*d* through which a length of web 102 can travel without contacting and "picking up" another fastener element 54 until the next vertex 117 of dauber 98*d* comes into alignment with anvil 98*c*, thereby creating the spacing between fastener elements for the present embodiments.

In some embodiments, fastener elements 54 may be joined to web 102 via ultrasonic bonding or thermal bonding, with an adhesive, and/or with any other suitable joining process and/or material. In some embodiments, the relation between the velocity of web 102 in machine direction 106 and the rate of rotation of spool 98*c* may be configured such that distance 68 exists between successive fastener elements 54 joined to web 102.

In alternative embodiments, a web 114 of material may include a plurality of fastener elements 54 removably disposed thereon. Respective fastener elements 54 on web 114 may be separated from each other by length 68. As web 114 is fed onto web 102, fastener elements 54 are joined to web 102 and thereby separated from web 114. For example, a bonding force between fastener elements 54 and web 102 is greater than a bonding force between fastener elements 54 and web 114.

Figure 4:
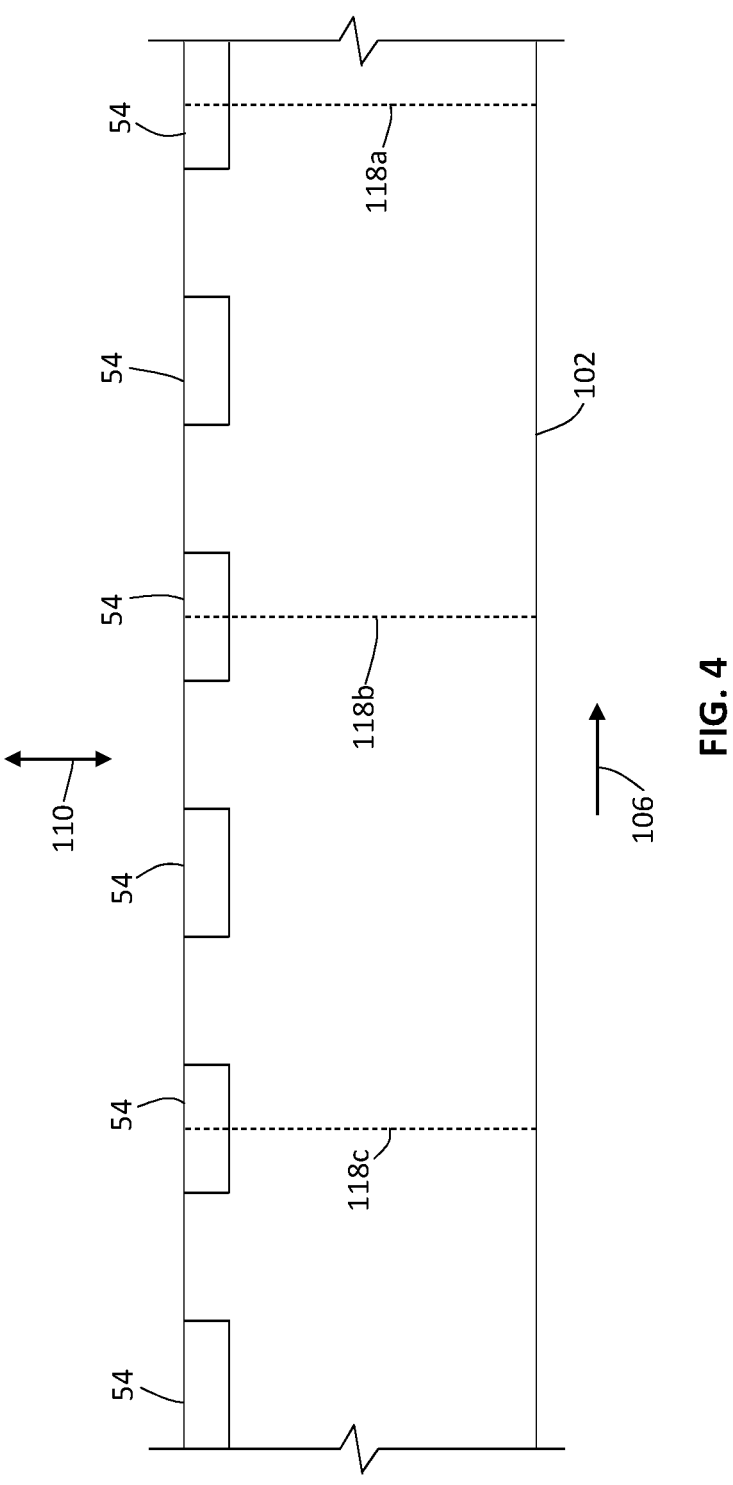
FIG. 4 is a schematic top view of a web of material configured to be cut into a plurality of fastener panels.
Figure 5:
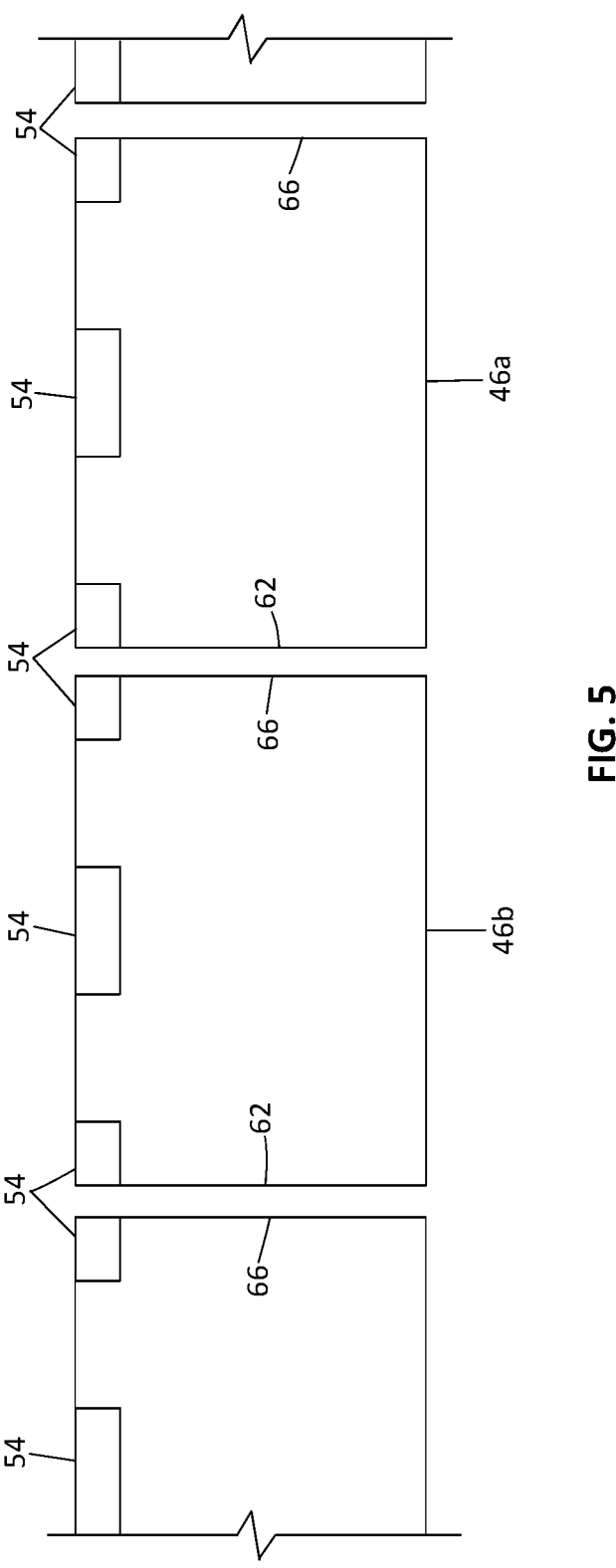
FIG. 5 is a schematic top view of the web of material of FIG. 4 after being cut into the plurality of fastener panels.

FIGS. 4 and 5 depict top views of web 102 after fastener elements 54 have been joined thereto. As shown, fastener elements 54 are arranged in a substantially straight line extending in machine direction 106. After fastener elements 54 are joined to web 102, web 102 is cut in cross-machine direction 110 using a blade 122, as shown in FIG. 3. For example, in some embodiments, blade 122 may reciprocate in direction 120 such that a cut is formed through web 102 in cross-direction 110. In some embodiments, the cut is formed through a portion of web 102 having a fastener element 54 thereon such that a fastener element 54 and the web are both cut in a single cutting action. For example, conveyor system 90 may include a blade configured to cut web 102 along respective imaginary lines 118*a-c*, each of which are parallel to cross-machine direction 110, as shown in FIG. 4. Each cut through web 102 defines one of the first end 62 and second end 66 of a respective fastener panel 46, as shown in FIG. 5. For example, cutting along line 118*a* (FIG. 4) through both fastener element 54 and web 102 at a first point along a length (e.g., extending in a direction parallel to machine direction 106) of web 102 thereby defines second end 66 (FIGS. 1 and 5) of a first fastener panel 46*a*. Thereafter, cutting along line 118*b* (FIG. 4) through both fastener element 54 and web 102 at a second point along the length of web 102 thereby defines first end 62 (FIGS. 1 and 5) of first fastener panel 46*a*. The cut along line 118*b* defining first end 62 of first fastener panel 46*a* may also define a second end 66 of a second fastener panel 46*b*, as shown in FIG. 5. Thereafter, successive cutting may be repeated along lines 118*c-n* through both a respective fastener element 54 and web 102, thereby defining one of first end 62 and second end 66 of the respective fastener panel 46.

In some embodiments, the cut is formed at a predetermined point or distance along length 70 of fastener element 54. In some embodiments, the predetermined point or distance is a percentage of length 70 of fastener element 54, such as 50%. For example, length 70 of third fastener element 54*c* is substantially equal to the sum of the lengths 70*a* of both first and second fastener elements 54*a*, 54*b*. Each fastener panel 46 may be cut to define any appropriate length 82, such as a length less than or equal to a length 86 of an outer edge 58 of first extension portion. For example, in some embodiments the cut is formed at a predetermined point or distance along length 70 of fastener element that is more than any one of, or between any two of: 20, 30, 40, 50, 60, and/or 70 percent of the length of the fastener element.

After the fastener elements 54 have been joined to web 102 and web 102 has been cut to define fastener panels 46, each fastener panel 46 may be joined to respective side of a chassis of article 10. For example, first fastener panel 46*a* may be joined to extension portion 42*a* on a first side of the chassis of article 10 and second fastener panel 46*b* may be joined to extension portion 42*a* on a second side of the chassis of article 10, which is opposite the first side.

The above-described embodiments include the benefits of increasing the structural integrity of the absorbent article during use, while avoiding or minimizing additional capital cost, material cost, and/or product waste.

Providing a distance between successive fastener elements 54 prevents manufacturing complications and reduces material costs. For example, running a continuous web of fastener elements 54 onto web 102 is complicated because running two different web materials on a production line may cause processing problems (e.g., buckling) and/or discomfort to the user during use (e.g., fastener element material may become exposed and dig into the user's skin). Furthermore, 33% less fastener element material is used when providing a one-inch distance between successive fastener elements 54 on fastener panel 46, as compared to using a continuous web of fastener elements 54 on fastener panel 46.

Providing a fastener element 54 at each end 62, 66 of fastener panel 46 increases the structural integrity of the article during use and avoids or minimizes additional capital and material costs. For example, fastener elements 54 at each end 62, 66 prevent detachment, such as by peeling, of fastener panel 46 from second extension portion 42*b* during use. Moreover, shifting the cutting phase, from cutting between respective fastener elements 54, to cutting through respective fastener elements 54, does not require additional manufacturing equipment and/or additional material.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A disposable absorbent article, comprising:
an absorbent article chassis is having opposing front and rear waist portions, and a central absorbent portion extending in a longitudinal direction between the front and rear waist portions,
a first fastener panel having a first edge coupled to a first side of the rear waist portion, and a second edge configured to overlap a first side of the front waist portion to define a first leg opening on a first side of the central absorbent portion;
a second fastener panel having a first edge coupled to a second side of the rear waist portion, and a second edge configured to overlap a second side of the front waist portion to define a second leg opening on a second side of the central absorbent portion; and
wherein the first and second fastener panels each comprise:
a first fastener element coupled to and overlapping the fastener panel at a first end of the fastener panel;
a second fastener element coupled to and overlapping the fastener panel at a second end of the fastener panel;
a third fastener element coupled to the fastener panel such that the third fastener element is in line and spaced apart from each of the first and second fastener elements along a length of the fastener panel; and
wherein:
each of the first, second, and third fastener elements are disposed along the second edge of each of the first and second fastener panels;
a length of the second fastener element is substantially equal to the sum of the lengths of a first and third fastener elements;
an edge of the first fastener element is coterminous with a third edge of the first fastener panel at the first end of the first fastener panel; and
an edge of the second fastener element is coterminous with a fourth edge of the first fastener panel at the second end of the first fastener panel.

2. The article of claim 1, wherein:
the third edge of the fastener panel extends from the first edge to the second edge in a straight line;
the fourth edge of the fastener panel extends from the first edge to the second edge in a straight line.

3. The article of claim 1, further comprising:
a first extension portion extending between and coupled to each of the first side of the rear waist portion and to the first edge of the first fastener panel; and a second extension portion extending between and coupled to each of the second side of the rear waist portion and the first edge of the second fastener panel; and
wherein the first fastener panel, the second fastener panel, the first extension portion, and the second extension portion are not integrally formed.

4. The article of claim 1, wherein the central absorbent portion is disposed on a user-facing surface of the absorbent article chassis.

5. The article of claim 1, wherein, for at least one of the first and second fastener panels, each of the first, second, and third fastener elements is disposed on a user-facing surface of the respective first and/or second fastener panel.

6. The article of claim 1, wherein each of the first, second, and third fastener elements are disposed along the second edge of each of the first and second fastener panels.

7. The article of claim 2, wherein the first fastener element is spaced apart from the second fastener element by a first distance, and the second fastener element is spaced apart from the third fastener element by a second distance that is substantially equal to the first distance.

8. The article of claim 1, wherein, for at least one of the first and second fastener panels, at least one of the first, second, and third fastener elements is disposed closer to the second edge than the first edge.

9. A disposable absorbent article, comprising:
an absorbent article chassis having a first end and an opposing second end, a first side and an opposing second side each extending between the first and second ends, and a longitudinally-extending centerline;
a first fastener panel coupled to the first side of the chassis and extending in a first direction away from the centerline, wherein the first fastener panel is disposed closer to the first end than the second end of the chassis;
a second fastener panel coupled to the second side of the chassis and extending in a second direction away from the centerline, wherein the second fastener panel is disposed closer to the first end than the second end of the chassis;
wherein each of the first and second fastener panels comprise:
a first fastener element disposed on a first edge of the fastener panel;
a second fastener element disposed on a second edge of the fastener panel;
a third fastener element disposed between the first and second fastener elements such that the third fastener element is spaced apart from each of the first and second fastener elements along a direction that is parallel to the centerline; and
wherein a length of the third fastener element is substantially equal to the sum of the lengths of a first and second fastener elements.

10. The article of claim 9, wherein the chassis includes a first extension portion extending in the first direction away from the centerline on the first side, wherein the first fastener panel is coupled to the first extension portion.

11. The article of claim 10, wherein the chassis includes a second extension portion extending in the second direction away from the centerline on the second side, wherein the second fastener panel is coupled to the second extension portion.

12. The article of claim 11, wherein the chassis includes a backsheet and each of the first and second extension portions are coupled to the backsheet.

13. The article of claim 12, wherein the chassis includes an absorbent portion extending along the centerline between the first and second ends of the chassis, wherein the absorbent portion is coupled to the backsheet.

14. The article of claim 9, wherein the first fastener panel is configured to overlap a first portion of the chassis proximate the second end to define a first leg opening on the first side of the chassis.

15. The article of claim 14, wherein the second fastener panel is configured to overlap a second portion of the chassis proximate the second end to define a second leg opening on the second side of the chassis.

16. The article of claim 14, wherein the chassis includes a third extension portion extending in the first direction away from the centerline on the first side, the third extension portion defining the first portion of the chassis configured to overlap with the first fastener panel.

17. The article of claim 15, wherein the chassis includes a fourth extension portion extending in the second direction away from the centerline on the second side, the fourth extension portion defining the second portion of the chassis configured to overlap with the second fastener panel.

18. The article of claim 9, wherein each of the first, second, and third fastener elements are disposed along a free edge of each of the first and second fastener panels.

19. The article of claim 9, wherein the first fastener element is spaced apart from the third fastener element by a first distance, and the third fastener element is spaced apart from the second fastener element by a second distance that is substantially equal to the first distance.

* * * * *